(12) United States Patent
Birck

(10) Patent No.: US 8,419,655 B2
(45) Date of Patent: Apr. 16, 2013

(54) METHOD AND APPARATUS FOR AURAL ACOUSTIC IMMITTANCE MEASUREMENT

(75) Inventor: Jonathan David Birck, Portland, OR (US)

(73) Assignee: JD Birck, LLC, Portland, OR (US)

( * ) Notice: Subject to any disclaimer, the term of this patent is extended or adjusted under 35 U.S.C. 154(b) by 446 days.

(21) Appl. No.: 12/586,609

(22) Filed: Sep. 23, 2009

(65) Prior Publication Data

US 2011/0071422 A1  Mar. 24, 2011

(51) Int. Cl.
*A61B 5/00* (2006.01)
(52) U.S. Cl.
USPC .......................................................... 600/559
(58) Field of Classification Search .................. 600/559, 600/561, 378, 544, 546; 73/573, 585, 589, 73/648; 181/135; 381/312; 128/898
See application file for complete search history.

(56) References Cited

U.S. PATENT DOCUMENTS

| | | | | | |
|---|---|---|---|---|---|
| 3,882,848 | A | * | 5/1975 | Klar et al. | 600/559 |
| 4,057,051 | A | * | 11/1977 | Kerouac | 600/559 |
| 4,079,198 | A | * | 3/1978 | Bennett | 600/559 |
| 4,688,582 | A | * | 8/1987 | Heller et al. | 600/559 |
| 5,601,091 | A | * | 2/1997 | Dolphin | 600/559 |
| 5,792,072 | A | * | 8/1998 | Keefe | 600/559 |
| 5,916,174 | A | * | 6/1999 | Dolphin | 600/559 |
| 6,110,126 | A | * | 8/2000 | Zoth et al. | 600/559 |
| 6,123,677 | A | * | 9/2000 | Heitmann et al. | 600/559 |
| 6,149,605 | A | * | 11/2000 | Christiansen | 600/559 |
| 6,231,521 | B1 | * | 5/2001 | Zoth et al. | 600/559 |
| 6,866,639 | B2 | * | 3/2005 | Causevic et al. | 600/559 |
| 6,974,421 | B1 | * | 12/2005 | Causevic et al. | 600/561 |
| 2005/0015018 | A1 | * | 1/2005 | Dolphin et al. | 600/559 |
| 2006/0074341 | A1 | * | 4/2006 | Causevic et al. | 600/561 |
| 2007/0112279 | A1 | * | 5/2007 | Iseberg et al. | 600/559 |
| 2007/0161924 | A1 | * | 7/2007 | Dolphin et al. | 600/559 |
| 2008/0194984 | A1 | * | 8/2008 | Keefe | 600/559 |
| 2009/0321177 | A1 | * | 12/2009 | McMahon et al. | 181/135 |

OTHER PUBLICATIONS

James Jerger. Phd; Clinical Experience With Impedance Audiometry: Arch Otolaryngology. Oct. 1970, pp. 311-324, vol. 92, iss. 4; U.S.A.
Gunnar Liden; The Scope and Application of Current Audiometric Tests: Journal of Laryngology and Otology, Jun. 1969, pp. 507-520, vol. 83, iss. 6.

* cited by examiner

*Primary Examiner* — Brian Szmal
(74) *Attorney, Agent, or Firm* — James G. Stewart PC

(57) ABSTRACT

An acoustic immittance measurement system converts a measure of acoustic immittance (i.e. impedance and/or admittance) of a subject's middle ear to the frequency domain such that variations in magnitude and/or phase are diagnosed using either open-loop or closed-loop measurement techniques.

20 Claims, 2 Drawing Sheets

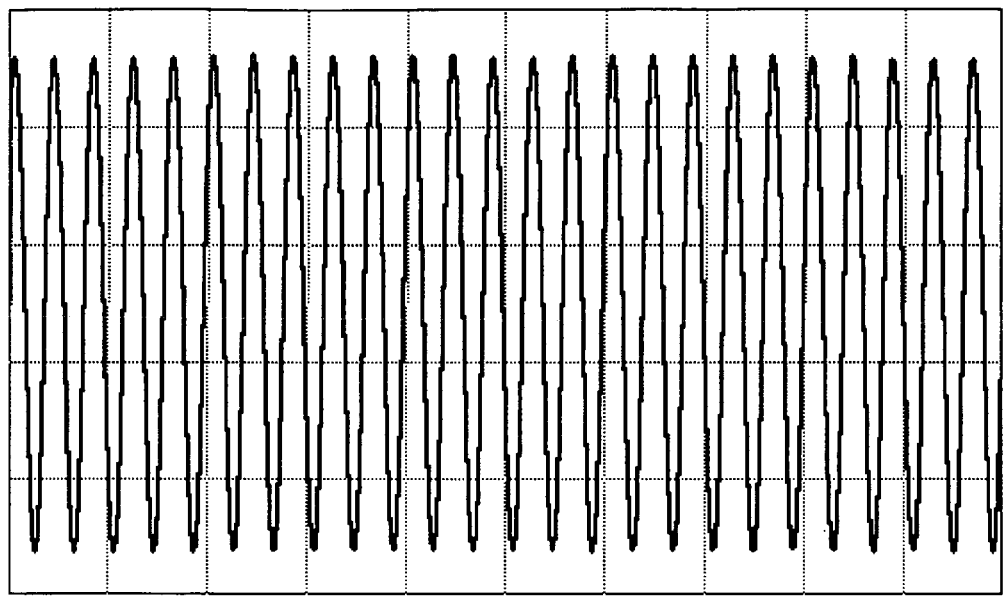
FIG. 2A  Time domain waveform
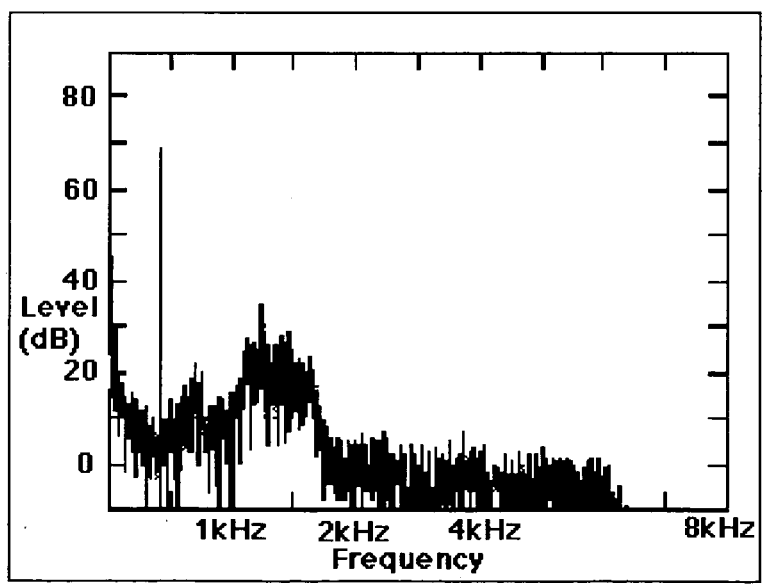
FIG. 2B  Frequency domain waveform

METHOD AND APPARATUS FOR AURAL ACOUSTIC IMMITTANCE MEASUREMENT

FIELD OF THE INVENTION

The invention relates generally to the field of audiologic testing, and more particularly to measures of impedance/admittance testing of the middle ear in animals or in humans.

BACKGROUND OF THE INVENTION

Those of skill in the art will understand acoustic immittance to be defined broadly herein as referring to either or both of acoustic impedance or its logical and numerical inverse, acoustic admittance. These two acoustic characteristics are characterized as being numerical inverses of one another in that an acoustic impedance measurement of 0.2 corresponds to an acoustic admittance measurement of 5.0. In other words, admittance=1/impedance and impedance=1/admittance. The invention is not so limited, however, to such a precise logical or mathematical construct, and the appended claims are intended broadly to cover acoustic impedance, admittance, and/or immittance, however measured or otherwise characterized.

The measurement of aural acoustic immittance has been performed for many years, and it is a routine that is common in the initial test battery run on patients who visit a physician with a complaint of ear problems. Generally this physician is one with a specialty in Ear Nose and Throat pathology. The test is commonly administered by an audiologist. Audiologists are people who are trained in the function, pathology and testing of ears. The specific types of equipment used to administer this test are commonly called 'impedance testers', 'admittance testers', or 'middle ear analyzers'.

Impedance testers commonly do a set of tests such as tympanometry, acoustic reflex test, acoustic reflex decay and Eustachian tube function tests. Primarily these tests are run to test the condition of the bones and ligaments between the tympanic membrane (eardrum) and the inner ear. The purpose of this 'middle ear' is to conduct energy received by the tympanic membrane through the air-filled middle ear to the fluid-filled inner ear, where it is separated into discrete frequency components and transduced into neural energy for conduction to the brainstem.

Test instruments used to make measurements on the middle ear typically measure the manner that it conducts the energy from the tympanic membrane to the inner ear. They measure the acoustic admittance using a probe with a plastic tip inserted into the ear canal. The plastic tip forms an air-tight seal in the ear canal. The air pressure typically is varied linearly (although alternative sweeps, e.g. a non-linear sweep that shortens test time, are sometimes used) in the ear canal from slight pressure to slight vacuum, and an acoustic test signal emitted from the probe will be measured using a microphone in the probe during this varying of the air pressure. When an electronic circuit is used to 'read' the microphone and then to vary the probe tone (the emitted pure tone) in order to keep the sound pressure level in the ear canal constant, the error correction signal in this feedback loop will be proportional to the acoustic admittance of the middle ear system. Both the magnitude and phase of this admittance can be measured, although it is common to measure and report only the magnitude of the measurement. Tympanometry is useful mainly to determine if there are problems with middle ear movement. See, for example, Liden, G., *The scope and application of current audiometric tests*, Journal of Laryngology and Otology, Volume 83, pp 507-520 (1969). Also see, for example, Jerger, J., *Clinical experience with impedance audiometry*. Archives of Otolaryngology, Volume 92, pp 311-324 (1970).

Originally these test instruments were stand-alone instruments, wholly contained stimulus and measurement instruments in one box that encompassed all necessary elements to perform the tests. These instruments had a power supply and derived their operating power directly from the power mains. In recent years these instruments have been connected to personal computers. A suitably programmed, special-purpose computer executing software instructions residing in memory, for example, can provide the user interface including a tympanographic display, provide for long-term storage of data, and even interface with other data stores such as patient management and billing systems. Although instruments have been computer-connected, they have kept their own power supplies and source energy directly from the mains supply.

Tympanometry is a measure of the components of stiffness of the middle ear and thus it evaluates middle ear function. This test can be helpful in detecting fluid in the middle ear, negative middle ear pressure, disruption of the ossicles, tympanic membrane perforation, and otosclerosis.

Tympanometry is also used for the evaluation of eustachian tube function. It is usually done by the same instrument that performs acoustic reflex testing.

Acoustic reflex testing consists of subjecting the ear to a loud pure tone or noise sound and determining whether and to what extent the sound causes the stapedius muscle to tighten the stapes. This in turn will stiffen the middle ear system, causing a measureable change in the impedance of that system. Acoustic reflexes are mainly useful as a non-subjective method of evaluating certain pathways from the ear to the brainstem and back, as the stapes should tighten for a sufficient level of sound. The absence of acoustic reflexes can be a sign of middle ear problems or of brainstem dysfunction.

To perform the tympanometry test, a probe with a soft plastic tip is placed into the ear canal. The plastic tip will seal the ear canal enabling the air pressure at the tympanic membrane to be varied. The air pressure in the sealed ear canal is varied in a systematic way from a small pressure to a small vacuum, or from vacuum to pressure, in a cyclic or loop technique that involves plural serial triple steps including measurements, computations, and adjustments, the cycle or loop being repeated until the measurement results finally converge. Conventional instruments use a microphone in the probe to measure the sound pressure level of a pure tone signal emitted by the probe and correct this sound pressure level so that it is held to a constant, unvarying value while the air pressure is changed. The error signal in this closed-loop correction system is directly proportional to the acoustic admittance of the middle ear system.

The result of the test conventionally is recorded in a visual output, called a tympanogram. If there is fluid in the middle ear, the middle ear system will not properly move freely, and the line on the tympanogram will be relatively flat. If there is air in the middle ear (the normal condition) but the air is at a higher or lower pressure than the surrounding atmosphere, the line on the tympanogram will be shifted to the left or right in position.

BRIEF DESCRIPTION OF THE DRAWINGS

FIGS. 2A and 2B are a pair of graphs illustrating the time (the upper trace of FIG. 2A) and frequency (the lower trace of FIG. 2B) domain measurements made possible in accordance with the invention. This brief description of FIGS. 2A and 2B are believed to be understood by those of ordinary skill in the art, without further explanation, to highlight the relative simplicity and ease of interpretation of the frequency-domain plot of FIG. 2B in accordance with the present invention over the relative difficulty or interpretation of the conventional time-domain plot of FIG. 2A.

DETAILED DESCRIPTION OF THE PREFERRED EMBODIMENTS

Figure 1:
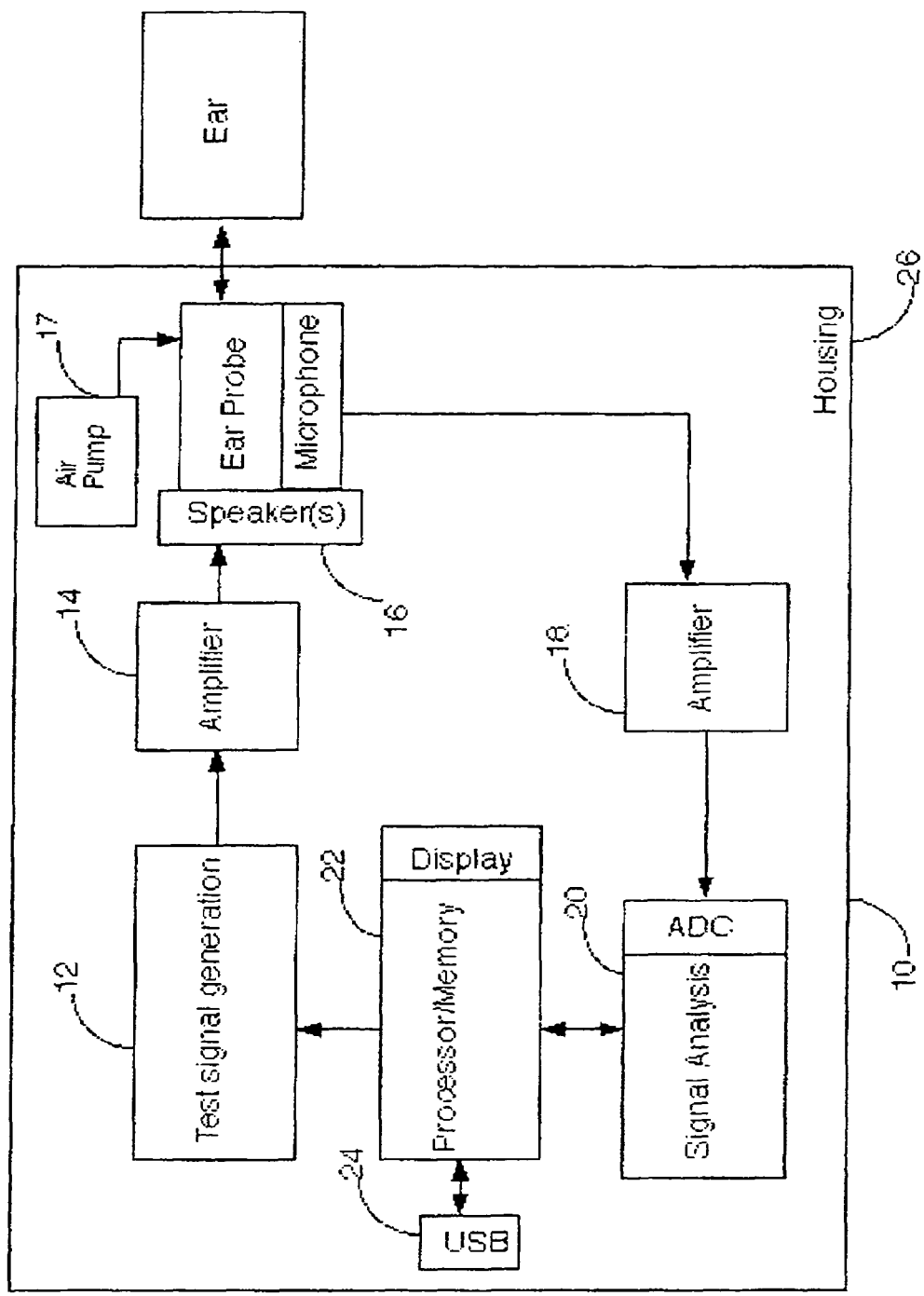
FIG. 1 is a system block diagram illustrating the various components coupled with one another in accordance with one embodiment of the system.

The present invention uses a completely different measurement methodology to make these same immittance measures. The new method has distinct advantages in making accurate measurements, and affords increased flexibility in test conditions while obtaining the measurements. Further, time arrangement of the measurement element relative to the computing element in the system has been dramatically altered. The instrument is configured within a small, lightweight housing in a manner that it need no longer be connected to the main power, but can derive its needed power from the computer across an industry-standard communications connection such as a universal serial bus (USB) port provided in the housing.

Using the above described invented measurement means, and the described architecture described in detail below, a highly flexible and accurate aural acoustic immittance measurement system can be realized that has unprecedented flexibility and convenience of use while maintaining useful and preferably superior measurement accuracy.

In contrast to the conventional method of using a closed-loop system to maintain the probe tone at a constant level in the ear canal, the invented method uses an open-loop system to make this measurement. In accordance with one embodiment of the system, the same pure tone is used as a measurement (probe) tone and the same microphone/speaker device that produces the probe tone (referred to herein as a speaker in keeping with its output function when producing the probe tone) is used as a receiver to measure the resulting sound pressure level in the ear canal. The input signal from the microphone is digitized using a high-resolution analog-to-digital (A/D) converter (ADC). This digitized waveform is then segmented into a precise number of samples and a Fourier Transform is performed on the waveform. The effect of the Fourier Transform is to take the time-domain set of samples and to calculate the frequency content of this time segment. The Fourier Transform is a well-known mathematical operation commonly used in non-medical fields such as communications systems.

After the Fourier Transform operation, the waveform contains the signal level of individual frequencies that are present in the acquired waveform segment sampled in the ear canal by the microphone. By observation of the frequency of the pure tone emitted by the probe, and by concurrent observation of the variation of this signal level during the air pressure sweep, the tympanogram may be recorded. This method removes limitations (e.g. dynamic range and response loop speed) and complexities (e.g. circuitry component count, and sensitivity to variation in temperature and component aging) of a closed-loop system.

During the acoustic reflex test a second pure tone or noise signal is introduced into the ear canal. Acoustic reflexes measure the stapedius and tensor tympani reflex in response to this second pure tone signal. Conventionally it is believed that the input to the acoustic reflex response (ACR) is hearing (8th nerve) and the output is the stapedius muscle (7th nerve) contraction. There is an ipsilateral (test ear is the same as the stimulated ear) and a contralateral (test ear is different from the stimulated ear) pathway. The ipsilateral pathway for the stapedius reflex goes into the $8^{th}$ cranial nerve from the inner ear, synapses in the ipsilateral cochlear nucleus, and then goes to the ipsilateral 7th nerve nucleus, and then to the stapedius. The contralateral pathway goes into the 8th nerve and synapses in the cochlear nucleus, but then is transferred across the trapezoid body to the superior olive, and then to the 7th nerve nucleus and to the stapedius.

The invention as described is useful to the impedance and/or admittance (i.e. immittance) measurement of the ACR in the same manner as it is used to make the impedance/admittance during tympanometry. While the nature of the measurement is the same as that for impedance/admittance (tympanometric), ACR requires higher resolution. For tympanometric measurements, it will be appreciated that a resolution of approximately 0.1 mmho is adequate, whereas for ACR, a significantly higher resolution of approximately 0.01 mmho is required.

Using the methods described herein affords much greater flexibility in making the ACR measure. Traditionally is has been very difficult to keep the pure tone signal used to elicit the ACR separate from the measurement (probe tone) signal, since it is desirable to measure the ACR at several different frequencies. When the acoustic reflex pure tone's frequency is near the measurement tone frequency, there can be corruption of the measurement due to the influence of the acoustic reflex tone. A sharp filter is required to be constructed in the measurement circuit, and this filter needs to be able to be moved from frequency to frequency. This is not an easy task.

Further to this difficulty of keeping the acoustic reflex stimulus from influencing the measurement is the desire to use a stimulus tone that is lower in frequency than the measurement tone. Instruments do not often allow this to be done since the circuitry is very difficult and costly to develop. When the measurement methodology of this invention is applied, it is a simple task to keep the acoustic reflex stimulus signal from influencing the measurement tones. Moreover, the stimulus and response are easily separated by virtue of the Fourier Transform technique, which relies on the frequency domain instead of the time domain.

Further to this invention is a method for increasing the accuracy of such a measurement. The probe tone is an electronic signal delivered to the speaker in the probe, which turns this electronic signal into an acoustic sound with a defined sound pressure level. The measurement performed by the microphone of the sound pressure level in the ear canal generates a signal that consists primarily of the signal delivered to the speaker in the probe. Those of skill in the art will appreciate that a so-called composite signal measured by the microphone includes a small (desirable and/or meaningful) signal riding on a large (undesirable and/or meaningless) signal. If the measurement system supplies this waveform to the amplifier that amplifies the microphone signal, then the amplifier uses this waveform to amplify the difference between it and the signal from the microphone in a manner such that the primary signal is cancelled at a specific level. (Effectively, the large unwanted or meaningless signal is subtracted out of the composite signal in a process step referred to herein as cancellation or an element referred to herein as a cancelling means.) Thus, amplification of only the wanted or meaningful composite signal component is obtained, resulting in a much lower-noise measurement (characterized by a higher signal-to-noise ratio (SNR) at much higher resolution.

Another version of this difference amplifier allows the phase of the reference signal to be changed in order to match the phase of the measured signal. By doing this, the amplifier can be increased in gain resulting in an improved measurement dynamic range, and in a higher (improved) SNR.

Additionally, the frequency of the measurement (probe) tone can be varied easily and tracked by observation of the waveform output from the Fourier Transform operation. Since the frequencies can be tracked individually, multiple frequencies can be tested at one time, thus simplifying the measurement when it is desired to perform the tympanometry test repeatedly at many frequencies. This is referred to herein as Multiple Frequency Tympanometry. A probe tone comprising one or more (e.g. a plurality) of pure tones, or of another tonal scheme, can be used and all can be tracked concurrently during one air pressure sweep, thus significantly shortening the test time and providing increased user and patient convenience and comfort. Accuracy is increased when all tympanograms are recorded in one air sweep, as the ear can change due to repeated air pressure sweeps. This is possible in accordance with the teachings of the present invention.

Similarly, the ACR can be tested concurrently with multiple measurement tones. This results in a more rapid test protocol in determining the ACR at different measurement frequencies.

Additionally, the stimulus tone for eliciting the ACR can be a pulsed tone with each pulse at a different sound pressure level, or it can be a stimulus tone or noise signal that is quickly swept either from a high-to-low pressure level or from a low-to-high pressure level (and either linearly or non-linearly, within the spirit and scope of the invention) thereby to measure the acoustic reflex threshold. This latter can shorten test times and improve user convenience and patient comfort.

Referring briefly now to FIG. 1, the elements and open-loop topology of invented system 10 will be summarized. System 10 may be seen to include a test signal generation block 12, an amplifier 14 operatively connected thereto, an ear probe 16 operatively connected thereto including therein one or more speaker(s), and a conventional air pump 17. This combination of elements may be referred to herein as a pump means. System 10 may be seen also to include ear probe 18 also including therein a microphone, a second amplifier 18 operatively coupled thereto, and a signal analysis block 20 including an analog-to-digital (A/D) converter (ADC) therein. This combination of elements may be referred to herein as a measuring means.

Referring still to FIG. 1, system 10 may be seen further to include a processor/memory block 22 including a display coupled therewith, the processor/memory block also operatively coupled to signal analysis block 20 and to test signal generation block 12 for controlling the supply of variable pressure stimulus to ear probe 16 and for monitoring and displaying a tympanogram representative of the subject's response tympanic membrane, middle ear, and otherwise audiologic/physiologic response thereto.

Those of skill in the art will appreciate that the components of invented system 10 including processor/memory block 22 obtain their DC power not from a power mains as with conventional and more complex instrumentation but instead from a standardized telecommunications port such as a universal serial bus (USB) port 24. Those of skill in the art will also appreciate that, in accordance with one embodiment of the invention, most or all such functional blocks reside within a small, lightweight housing 26, thus simplifying and miniaturizing and rendering largely self-contained aural acoustic immittance measurement system 10 relatively inexpensive and portable.

Those of skill will appreciate that the pump means, within the spirit and scope of the invention, can be automatic and within housing 26, or can be manual and external thereto. This alternative configuration would further conserve DC power consumed by system 10 when such power is supplied from an external source, e.g. a laptop computer, connected to system 10 via a telecommunication port, e.g. USB port 24. Still, those of skill in the art will appreciate that the analysis of the response (and optional presentation thereof in suitable form via a display, for example) to such a sound stimulus—whether supplied to the ear via manual or automatic pump means—is in the frequency domain rather than the time domain, in accordance with the invention.

Those of skill in the art will appreciate that the invented method involves steps that correspond with acoustic immittance measurement systems described and illustrated herein, wherein, for example, one or more functional components of the system correspond with one or more functional steps of the method. Those of skill in the art will appreciate that one or more functional components of the invented system, or one or more functional steps of the invented method can be combined, omitted, or augmented, as contemplated, yet within the spirit and scope of the invention.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

I claim:

1. A system for measuring aural acoustic immittance comprising:
    an insertion probe including an air pump, the probe configured for insertion into the an external ear canal such that an airtight seal is obtained wherein an air pressure within an ear canal interior of the probe is capable of being varied;
    at least one speaker in the probe for producing a measurement sound in the ear canal;
    a microphone in the probe for producing a measurement signal of a sound pressure level in the sealed ear canal;

a signal generator and an amplifier operatively coupled with the air pump of the probe, the signal generator, the amplifier, and the air pump being collectively configured to vary an air pressure through the probe;

a measurement means for producing a measurement of an immittance of a middle ear beyond the external ear canal, whereby a measured signal is converted to a frequency domain and a measured value is recorded in a measurement system.

2. The system of claim 1, wherein the measurement signal is a single frequency and the measured value is a single frequency.

3. The system of claim 1, wherein the measurement signal is a set of multiple single frequencies and the measurement is a measure of values at more than one frequency.

4. The system of claim 1, wherein the measurement signal is a composite signal made of many frequencies and/or varying values, and the measurement is a measure of values at many frequencies.

5. The system of claim 1, wherein the measurement system is an open-loop measurement system.

6. A system for measuring aural acoustic immittance, the system comprising:
   an insertion probe configured for insertion into an external ear canal such that an airtight seal is obtained;
   a first speaker in the probe for producing a measurement sound in the ear canal;
   a microphone in the probe for producing a measurement signal of a sound pressure level in the sealed ear canal;
   a test signal generator, an amplifier, and an air pump operatively coupled with one another, the operatively coupled test signal generator, amplifier, and air pump being further operatively coupled with the probe and suitably configured to create a varying air pressure through the probe;
   a second speaker in the probe for producing a stimulus sound for eliciting an anatomical response;
   a second amplifier operatively coupled with the microphone and further coupled with an analog-to-digital converter configured to measure the immittance of a middle ear beyond the external ear canal, whereby a measured signal is converted to a frequency domain and a measured value is in recorded-a measurement system.

7. The system of claim 6, wherein thea test performed is an acoustic reflex response (ACR) test, wherein the anatomical response is an ACR, wherein the first speaker provides the measurement signal, wherein the second speaker provides the stimulus signal for eliciting the ACR, and wherein the microphone receives an acoustic signal from the sealed ear canal.

8. The stem of claim 7, wherein the stimulus sound for eliciting the ACR is a pulse of sound at a constant value of sound pressure level.

9. The system of claim 7, wherein the stimulus sound for eliciting the ACR is a pulse of sound or a continuous presentation of sound whereby a value of sound pressure varies with time, and wherein the continuous presentation of sound includes one pulse or a sequence of plural pulses.

10. The system of claim 6, wherein the measurement signal is a single frequency and the measured signal is a single frequency.

11. The system of claim 6, wherein the measurement signal is a set of multiple single frequencies and the measurement is a measure of one or more values at more than one frequency.

12. The system of claim 6, wherein the measurement signal is a composite signal made of many frequencies and/or varying values, and wherein the measurement is a measure of a plurality of values at a plurality of frequencies.

13. The system of claim 6, wherein the measurement system is an open-loop measurement system.

14. A system for measuring aural acoustic immittance comprising:
    an insertion probe configured for insertion into an external ear canal such that an airtight seal is obtained;
    one or more speakers in the probe configured to produce a measurement sound in the ear canal;
    a microphone in the probe configured to produce a measurement signal of a sound pressure level in the sealed ear canal;
    a pump means including a signal generator, an amplifier and an air pump coupled with the probe, the pump means configured to vary air pressure through the probe; and
    a measuring means for measuring the immittance of a middle ear beyond the external ear canal, whereby a measured signal is converted to a frequency domain and a measured value is recorded in a measurement system.

15. The system of claim 14 which further comprises:
    a direct current (DC) power source configured to supply power to at least the measuring means; and
    a housing containing at least the measuring means.

16. The system of claim 15, wherein the pump means is automatic, wherein the DC power source is configured also to supply power to the pump means, and wherein the housing further contains the pump means.

17. The system of claim 16 further comprising:
    a display configured on the housing for visually indicating the measured aural acoustic immittance.

18. The system of claim 15, wherein the pump means is manual and is external to the housing.

19. The system of claim 18, wherein the display features a tympanogram.

20. The system of claim 15, wherein the DC power source is external to the housing and supplies DC power via a communications interface port provided on the housing.

* * * * *